US009702885B2

(12) United States Patent
Walker et al.

(10) Patent No.: US 9,702,885 B2
(45) Date of Patent: Jul. 11, 2017

(54) RECOMBINANT DEAMIDATED GLIADIN ANTIGEN

(71) Applicant: Bio Rad Laboratories, Inc., Hercules, CA (US)

(72) Inventors: Roger Walker, Benicia, CA (US); Yabin Lu, Pleasanton, CA (US); Urvee Desai, San Ramon, CA (US); Daming Shan, Shoreline, WA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 895 days.

(21) Appl. No.: 13/692,938

(22) Filed: Dec. 3, 2012

(65) Prior Publication Data

US 2013/0288274 A1   Oct. 31, 2013

Related U.S. Application Data

(60) Provisional application No. 61/567,060, filed on Dec. 5, 2011.

(51) Int. Cl.
| | |
|---|---|
| *G01N 33/68* | (2006.01) |
| *C12N 9/10* | (2006.01) |
| *C07K 14/415* | (2006.01) |
| *G01N 33/564* | (2006.01) |

(52) U.S. Cl.
CPC ....... *G01N 33/6893* (2013.01); *C07K 14/415* (2013.01); *C12N 9/1044* (2013.01); *C12Y 203/02013* (2013.01); *G01N 33/564* (2013.01); *C07K 2319/21* (2013.01); *C07K 2319/23* (2013.01); *G01N 2800/06* (2013.01)

(58) Field of Classification Search
None
See application file for complete search history.

(56) References Cited

U.S. PATENT DOCUMENTS

| | | | |
|---|---|---|---|
| 6,613,530 B1 | 9/2003 | Wienhues et al. | |
| 2004/0023848 A1 | 2/2004 | Boehm | |
| 2006/0240475 A1 | 10/2006 | Khosla et al. | |
| 2007/0161081 A1 | 7/2007 | Jin et al. | |
| 2009/0156490 A1 | 6/2009 | Khosla et al. | |
| 2009/0176251 A1 | 7/2009 | Binder et al. | |
| 2009/0311727 A1 | 12/2009 | Watkins et al. | |
| 2010/0203558 A1 | 8/2010 | Probst et al. | |
| 2010/0297607 A1* | 11/2010 | Zheng | G01N 33/5767 435/5 |
| 2012/0214200 A1* | 8/2012 | Grossmann | C07K 14/775 435/68.1 |

FOREIGN PATENT DOCUMENTS

| | | |
|---|---|---|
| WO | 02/083722 A2 | 10/2002 |
| WO | 2004/045392 A2 | 6/2004 |
| WO | 2009/131909 A2 | 10/2009 |
| WO | 2013/085851 A2 | 6/2013 |

OTHER PUBLICATIONS

Aleanzi, M. et al., "Celia disease: antibody recognition against native and selectively deamidated gliadin peptides," Clinical Chemistry, American Association for Clinical Chemistry, Washington, DC, vol. 47, No. 11, Nov. 1, 2001, pp. 2023-2028.
Colman, P.M., "Effects of amino acid sequence changes on antibody-antigen interactions," Research in Immunology, 1994, 145(1):33-36.
Dieterich et al., "Cross linking to tissue transglutaminase and collagen favours gliadin toxicity in coeliac disease," Gut, Apr. 2006, vol. 55, No. 4, pp. 478-484.
Dieterich et al., "Cross linking to tissue transglutaminase and collagen favours gliadin toxicity in coeliac disease," Gut, Apr. 2006, vol. 55, No. 4, pp. 478-484. Abstract only; [online], provided to verify the publication date for Dieterich, cite No. 20.
Harlow, E. et al., Antibodies: A Laboratory Manual (1998) Cold Spring Harbor Laboratory Press, Cold Spring Harbor, NY, pp. 23-26.
Karlin & Altschul, Proc. Nat'l. Acad. Sci. USA 90:5873-5787 (1993).
Kasperkiewicz, M. et al., "Novel assay for detecting celiac disease-associated autoantibodies in dermatitis herpetiformis using deamidated gliadin-analogous fusion peptides," Journal of the American Academy of Dermatology, 2012, Mosby Inc. USA, vol.
Lederman et al., "A single amino acid substitution in a common African allele of the CD4 molecule ablates binding of the monoclonal antibody, OKT4," Mol Immunol, Nov. 1991, 28(11):1171-1181.
Mothes, Thomas, "Deamidated gliadin peptides as targets for celiac disease-specific antibodies," Advances in Clinical Chemistry, Academic Press, London, GB, vol. 44, Jan. 1, 2007, pp. 35-63. 66, No. 4, Aug. 16, 2011, pp. 583-588.
Prause, Christian et al., "New developments in serodiagnosis of childhood celiac disease assay of antibodies against deamidated gliadin," Contemporary Challenges in Autoimmunity, Blackwell Publishing, Oxford, UK: Annals of the New York Academy of Sciences, 2009, pp. 28-35, & 6th International Congress on Autoimmunity, Oporto, Portugal, Sep. 10-14, 2008.
Wear et al., "A surface plasmon resonance-based assay for small molecule inhibitors of human cyclophilin A," Analytical Biochemistry, 345 (2005) 214-226.

(Continued)

*Primary Examiner* — Christine Foster
(74) *Attorney, Agent, or Firm* — Kilpatrick Townsend & Stockton LLP

(57) ABSTRACT

The present invention provides a method for determining whether a subject is suffering from celiac disease by contacting a sample of bodily fluid from the subject, with an antigen formed from a hexamer of a gliadin fusion protein immobilized on a solid support. The gliadin fusion protein of the antigen includes a recombinant deamidated gliadin linked to a tag such as Glutathione-S transferase (GST) protein. The antigen is prepared by immobilizing the gliadin fusion protein on the solid support. The antigen can further include tissue Transglutaminase (tTG) cross-linked to the gliadin fusion protein. When tTG is present, the tTG and recombinant deamidated gliadin are mixed together prior to immobilization to the solid phase.

8 Claims, 4 Drawing Sheets

(56) References Cited

OTHER PUBLICATIONS

Dobson, "The Generic Nature of Protein Folding and Misfolding", Protein Misfolding, Aggregation and Conformational Diseases Part A: Protein Aggregation and Conformational Diseases, Uversky and Fink (Eds.), 2006, Springer, pp. 21-41.
Hernandez Marin, et al., "Chimeric synthetic peptides as antigens for detection of antibodies to *Trypanosoma cruzi*", Biochemical and Biophysical Research Communications 339 (2006) pp. 89-92.
Zhang, "Protein structure prediction: when is it useful?", Current Opinion in Structural Biology 19(2009):145-155.
EP12855209.8 , "Extended European Search Report", Jun. 12, 2015, 7 pages.
PCT/US2012/067639 , "International Search Report & Written Opinion", Mar. 5, 2013, 9 pages.

\* cited by examiner

SEQUENCE LISTING

```
<160> NUMBER OF SEQ ID NOS: 15

<210> SEQ ID NO 1
<211> LENGTH: 16
<212> TYPE: PRT
<213> ORGANISM: Artificial Sequence
<220> FEATURE:
<223> OTHER INFORMATION: synthetic gliadin protein D2 peptide

<400> SEQUENCE: 1

Gln Pro Glu Gln Pro Gln Gln Ser Phe Pro Glu Gln Glu Arg Pro Phe
 1               5                  10                  15

<210> SEQ ID NO 2
<211> LENGTH: 5
<212> TYPE: PRT
<213> ORGANISM: Artificial Sequence
<220> FEATURE:
<223> OTHER INFORMATION: synthetic peptide spacer, glycine-serine
      polymer spacer, flexible linker

<400> SEQUENCE: 2

Gly Gly Gly Gly Ser
 1               5

<210> SEQ ID NO 3
<211> LENGTH: 121
<212> TYPE: PRT
<213> ORGANISM: Artificial Sequence
<220> FEATURE:
```

<223> OTHER INFORMATION: synthetic recombinant gliadin protein D2
      hexamer

<400> SEQUENCE: 3

Gln Pro Glu Gln Pro Gln Ser Phe Pro Glu Gln Glu Arg Pro Phe
1               5                   10                  15

Gly Gly Gly Gly Ser Gln Pro Glu Gln Pro Gln Ser Phe Pro Glu
            20                  25                  30

Gln Glu Arg Pro Phe Gly Gly Gly Gly Ser Gln Pro Glu Gln Pro Gln
        35                  40                  45

Gln Ser Phe Pro Glu Gln Glu Arg Pro Phe Gly Gly Gly Gly Ser Gln
        50                  55                  60

Pro Glu Gln Pro Gln Gln Ser Phe Pro Glu Gln Glu Arg Pro Phe Gly
65                  70                  75                  80

Gly Gly Gly Ser Gln Pro Glu Gln Pro Gln Gln Ser Phe Pro Glu Gln
                85                  90                  95

Glu Arg Pro Phe Gly Gly Gly Gly Ser Gln Pro Glu Gln Pro Gln Gln
                100                 105                 110

Ser Phe Pro Glu Gln Glu Arg Pro Phe
        115                 120

<210> SEQ ID NO 4
<211> LENGTH: 6
<212> TYPE: PRT
<213> ORGANISM: Artificial Sequence
<220> FEATURE:
<223> OTHER INFORMATION: synthetic His-tag

<400> SEQUENCE: 4

His His His His His His
1               5

<210> SEQ ID NO 5
<211> LENGTH: 15
<212> TYPE: PRT
<213> ORGANISM: Artificial Sequence
<220> FEATURE:
<223> OTHER INFORMATION: synthetic His-tag

<400> SEQUENCE: 5

Met Arg Gly Ser His His His His His His Gly Ser Pro Glu Phe
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic His-tag

<400> SEQUENCE: 6

Met Arg Gly Ser His His His His His His Gly Ser Pro Lys Phe
1               5                   10                  15

<210> SEQ ID NO 7
<211> LENGTH: 136
<212> TYPE: PRT
<213> ORGANISM: Artificial Sequence
<220> FEATURE:
<223> OTHER INFORMATION: synthetic "classic" D2 hexamer with His tag,
      classic His-tagged recombinant deaminated gliadin protein (DGP)

<400> SEQUENCE: 7

Met Arg Gly Ser His His His His His Gly Ser Pro Glu Phe Gln
1               5                   10                  15

Pro Glu Gln Pro Gln Gln Ser Phe Pro Glu Gln Glu Arg Pro Phe Gly
            20                  25                  30

Gly Gly Gly Ser Gln Pro Glu Gln Pro Gln Gln Ser Phe Pro Glu Gln
        35                  40                  45

Glu Arg Pro Phe Gly Gly Gly Ser Gln Pro Glu Gln Pro Gln Gln
50                  55                  60

Ser Phe Pro Glu Gln Glu Arg Pro Phe Gly Gly Gly Ser Gln Pro
65                  70                  75                  80

Glu Gln Pro Gln Gln Ser Phe Pro Glu Gln Glu Arg Pro Phe Gly Gly
            85                  90                  95

Gly Gly Ser Gln Pro Glu Gln Pro Gln Gln Ser Phe Pro Glu Gln Glu
            100                 105                 110

Arg Pro Phe Gly Gly Gly Gly Ser Gln Pro Glu Gln Pro Gln Gln Ser
            115                 120                 125

Phe Pro Glu Gln Glu Arg Pro Phe
            130                 135

<210> SEQ ID NO 8
<211> LENGTH: 136
<212> TYPE: PRT
<213> ORGANISM: Artificial Sequence
<220> FEATURE:
<223> OTHER INFORMATION: synthetic "lysine-containing" D2 hexamer with
      His tag, His-tagged recombinant deaminated gliadin
      protein with lysine substituted at position 14

<400> SEQUENCE: 8

Met Arg Gly Ser His His His His His Gly Ser Pro Lys Phe Gln
1               5                   10                  15

Pro Glu Gln Pro Gln Gln Ser Phe Pro Glu Gln Glu Arg Pro Phe Gly
            20                  25                  30

Gly Gly Gly Ser Gln Pro Glu Gln Pro Gln Gln Ser Phe Pro Glu Gln
        35                  40                  45

Glu Arg Pro Phe Gly Gly Gly Ser Gln Pro Glu Gln Pro Gln Gln
50                  55                  60

Ser Phe Pro Glu Gln Glu Arg Pro Phe Gly Gly Gly Ser Gln Pro
65                  70                  75                  80

Glu Gln Pro Gln Gln Ser Phe Pro Glu Gln Glu Arg Pro Phe Gly Gly
            85                  90                  95

Gly Gly Ser Gln Pro Glu Gln Pro Gln Gln Ser Phe Pro Glu Gln Glu
            100                 105                 110

Arg Pro Phe Gly Gly Gly Gly Ser Gln Pro Glu Gln Pro Gln Gln Ser
            115                 120                 125

Phe Pro Glu Gln Glu Arg Pro Phe
            130                 135

<210> SEQ ID NO 9
<211> LENGTH: 366
<212> TYPE: DNA
<213> ORGANISM: Artificial Sequence
<220> FEATURE:
<223> OTHER INFORMATION: synthetic recombinant gliadin protein D2
      hexamer

<400> SEQUENCE: 9
cagcccgaac aaccgcaaca atcattcccc gagcaagaaa ggccgttcgg tggcggtggc    60

-continued

```
tcgcagcccg aacaaccgca acaatcattc cccgagcaag aaaggccgtt cggtggcggt    120
ggctcgcagc ccgaacaacc gcaacaatca ttccccgagc aagaaaggcc gggtggcggt    180
ggctcggaat ccagcccga acaaccgcaa caatcattcc ccgagcaaga aaggccgttc    240
ggtggcggtg gctcgcagcc cgaacaaccg caacaatcat tccccgagca agaaaggccg    300
ttcggtggcg gtggctcgca gcccgaacaa ccgcaacaat cattccccga gcaagaaagg    360
ccgttc                                                               366
```

<210> SEQ ID NO 10
<211> LENGTH: 224
<212> TYPE: PRT
<213> ORGANISM: Artificiial Sequence
<220> FEATURE:
<223> OTHER INFORMATION: synthetic glutathione S-transferase (GST) protein

<400> SEQUENCE: 10

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

<210> SEQ ID NO 11
<211> LENGTH: 282
<212> TYPE: PRT
<213> ORGANISM: Artificiial Sequence
<220> FEATURE:
<223> OTHER INFORMATION: synthetic gliadin fusion protein including GST and recombinant deaminated gliadin D2 hexamer

<400> SEQUENCE: 11

```
Met Ser Pro Ile Leu Gly Tyr Trp Lys Ile Lys Gly Leu Val Gln Pro
1               5                   10                  15
```

```
Thr Arg Leu Leu Leu Glu Tyr Leu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
210                 215                 220

Gln Pro Glu Gln Pro Gln Gln Ser Phe Pro Glu Gln Glu Arg Pro Phe
225                 230                 235                 240

Gly Gly Gly Gly Ser Gln Pro Glu Gln Pro Gln Ser Phe Pro Glu
                245                 250                 255

Gln Glu Arg Pro Phe Gly Gly Gly Ser Gln Pro Glu Gln Pro Gln
            260                 265                 270

Gln Ser Phe Pro Glu Gln Glu Arg Pro Phe
            275                 280

<210> SEQ ID NO 12
<211> LENGTH: 16
<212> TYPE: PRT
<213> ORGANISM: Artificiial Sequence
<220> FEATURE:
<223> OTHER INFORMATION: synthetic variants of gliadin protein D2
      peptide
<220> FEATURE:
<221> NAME/KEY: VARIANT
<222> LOCATION: (1)...(13)
<223> OTHER INFORMATION: at least one Glx is Gln and at least one Glx
      is Glu

<400> SEQUENCE: 12

Glx Pro Glx Glx Pro Glx Glx Ser Phe Pro Glx Glx Arg Pro Phe
 1               5                  10                  15

<210> SEQ ID NO 13
<211> LENGTH: 5
<212> TYPE: PRT
<213> ORGANISM: Artificiial Sequence
<220> FEATURE:
<223> OTHER INFORMATION: synthetic peptide spacer, glycine-serine
      polymer spacer, flexible linker, repaeted an undefined
      number of times, (GGGGS)n
```

```
<400> SEQUENCE: 13

Gly Gly Gly Gly Ser
 1               5

<210> SEQ ID NO 14
<211> LENGTH: 5
<212> TYPE: PRT
<213> ORGANISM: Artificiial Sequence
<220> FEATURE:
<223> OTHER INFORMATION: synthetic peptide spacer, glycine-serine
      polymer spacer, flexible linker, repaeted an undefined
      number of times, (GSGGS)n

<400> SEQUENCE: 14

Gly Ser Gly Gly Ser
 1               5

<210> SEQ ID NO 15
<211> LENGTH: 4
<212> TYPE: PRT
<213> ORGANISM: Artificiial Sequence
<220> FEATURE:
<223> OTHER INFORMATION: synthetic peptide spacer, glycine-serine
      polymer spacer, flexible linker, repaeted an undefined
      number of times, (GGGS)n

<400> SEQUENCE: 15

Gly Gly Gly Ser
 1
```

RECOMBINANT DEAMIDATED GLIADIN ANTIGEN

CROSS-REFERENCES TO RELATED APPLICATIONS

This application claims the benefit of priority to U.S. Provisional Patent Application No. 61/567,060, filed Dec. 5, 2011, the entire content of which is incorporated by reference herein for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-939-1.TXT, created on Nov. 28, 2012, 12,288 bytes, machine format IBM-PC, MS-Windows operating system, is hereby incorporated by reference in its entirety for all purposes.

BACKGROUND OF THE INVENTION

Celiac disease (CD) is a severe gastrointestinal disease that has a strong genetic component. CD is characterized by a permanent intolerance of proteins from wheat, barley, rye, and oats. Although the physiopathology of CD is not completely understood it is clear that the presence of the toxic proteins in the patient's diet causes a total or partial damage of intestinal mucosa (Brandtzaeg, P. 1997. Mechanisms of gastrointestinal reactions to food. Environmental Toxicology and Pharmacology 4; 9-24) leading to severe malabsorption syndromes and causing diarrhea, vomiting, abdominal pain, anorexia, retarded growth, malnutrition and anemia. CD has been associated with a higher risk for intestinal cancer in non-diagnosed and untreated patients (Holmes G K T, 1989. Malignancy in coeliac disease-effect of a gluten-free diet, Gut 30; 333-338). CD affects mainly children under three years old, but it is also common in adults, and sometimes is clinically atypical or asymptomatic (Ferguson A, et al. 1992. Definitions and diagnostic criteria of latent and potential coeliac disease. Ed by Aurricchio 5, Visakorpi J K, in Epidemiology of CD. Dyn Nutr Res, Basel, Karger 2; 119-127). CD is more frequent in patients with other genetic or autoimmune disease, such as insulin dependent diabetes mellitus, Down syndrome, selective IgA deficiency, and dermatitis herpetiformis (Sirgus N et al. 1993. Prevalence of coeliac disease in diabetic children and adolescents in Sweden. Acta Pediatr 66; 491-494; Zubiliaga P et al. 1993. Down syndrome and coeliac disease. J Pediatr Gastroenterol Nutr 16:168-171; Boyce N 1997).

The clinical symptoms of CD could be confused with those produced by other gastrointestinal diseases. In these cases CD is misdiagnosed and patients do not receive the specific treatment, that is, a complete elimination of gluten in their diet. On the other hand, if a non-celiac patient is wrongly diagnosed as celiac, he would undergo an unnecessary gluten free diet for his whole life. Accordingly, a precise diagnosis of CD is essential. Currently the standard for CD diagnosis is intestinal biopsy, repeated three times: at the onset of the clinical symptoms, after several months on a gluten free diet, and after a challenge with gluten.

Because intestinal biopsy is an invasive method and precise serological tests have been developed, the above criteria have been revised (Walker-Smith et al. 1990. Revised criteria for diagnosis of coeliac disease. Report of Working group of European Society of Pediatric Gastroenterology and Nutrition. Arch Dis Child 65:909-911). Currently, serological tests can be done at the onset of clinical symptoms and when they are positive, a confirmatory intestinal biopsy will be indicated. The response to the treatment with a gluten-free diet can also be followed by serological tests. If discrepancies occur between the clinical response to the treatment and the result of serological tests a second intestinal biopsy would be indicated. Several serological tests have been developed for celiac disease diagnosis, such as the detection of antibodies to cellular antigens, or antibodies to food antigens, like gliadins. There are diagnostic kits for the detection of anti-endomysial antibodies, anti-reticulin antibodies, anti-gliadin antibodies, and anti-tissue transglutaminase antibodies.

Anti-gliadin antibodies (AGA) have been extensively used for serological diagnosis of CD (Stern M et al. 1996. Validation and standardization of serological screening tests for coeliac disease in 1996. 3rd EMRC/ESPGAN Workshop, Dec. 5-8, 1996, Molsheim, France, pp: 9-24; Catassi C et al. 1999. Quantitative antigliadin antibody measurement in clinical practice: an Italian multicenter study. Ital J Gastroenterol Hapatol 31; 366-370). AGA are mainly detected by ELISA (Enzyme-Linked Immunosorbent Assay), a simpler, more objective method than IFA (indirect immunofluorescent antibody analysis), and can be used for the analysis of a large number of samples. Nevertheless AGA are less specific for CD than endomysal antibodies (EMA) and the detection of antibodies to either IgA or IgG isotypes requires two independent assays. Recently a visual immunoassay for the detection of AGA, which solves some of these problems, has been reported (Garrote J A, Sorell L, Alfonso P et al 1999. A simple visual immunoassay for the screening of coeliac disease. Eur. J Clin Invest 29; 697-699; Spanish Office for Patents and Marks No. 9801067).

In 1997, Dietrich et al. identified tissue transglutaminase (tTG), an 85 kDa protein, as the major auto antigen detected by anti-endomysial antibodies (Dietrich W et al. 1997. Identification of tissue transglutaminase as the auto antigen of celiac disease. Nat Med. 3:797-801). Detection of anti-tTG antibodies had been reported lately in ELISA or radio-ligand (RLA) formats based on tTG from guinea pig liver extracts or recombinant human tTG cloned from different tissues (Sulkanen S et al. 1998. Tissue transglutaminase autoantibody enzyme-linked immunosorbent assay in detecting celiac disease. Gastroenterology 115:1322-1328; Siessler J et al. 1999. Antibodies to human recombinant tissue transglutaminase measured by radioligand assay: Evidence for high diagnostic sensitivity for celiac disease. Horm Metab Res 31; 375-379).

Prior art methods for detection of celiac disease use specific gliadin epitopes or pieces of the gliadin protein in an assay, that lead to both false-negatives and false-positives. What is needed is an assay that provides new antigens containing a more inclusive set of epitopes that provides a more accurate assay for celiac disease. Surprisingly, the present invention meets this and other needs.

SUMMARY OF THE INVENTION

In one embodiment, the present invention provides an antigen for detecting celiac disease. The antigen includes a recombinant deamidated gliadin having a hexamer of peptides each having SEQ ID NO:1, wherein the recombinant deamidated gliadin is covalently linked to a tag to form a gliadin fusion protein, wherein the gliadin fusion protein is immobilized on a solid support, and wherein the recombinant deamidated gliadin is capable of binding, to anti-deamidated gliadin antibodies.

In other embodiments, the present invention provides an antigen for detecting celiac disease prepared by the process including contacting a solid support with a gliadin fusion protein, wherein the gliadin fusion protein includes a recombinant deamidated gliadin having a hexamer of peptides each having SEQ ID NO:1 and wherein the recombinant deamidated gliadin is covalently linked to a tag, such that the gliadin fusion protein is immobilized on the solid support. Thus, the antigen for detecting celiac disease is prepared.

In some other embodiments, the present invention provides a method for diagnosing celiac disease in a subject. The method includes contacting a sample of bodily fluid from the subject with an antigen of the present invention, including a recombinant deamidated gliadin comprising a hexamer of SEQ ID NO:3. The method also includes detecting any antibody that has become specifically bound to the antigen, thus indicating the presence of celiac disease in the subject.

In another embodiment, the present invention provides a kit including an antigen of the present invention, wherein the recombinant deamidated gliadin includes a hexamer of SEQ ID NO:3, a detection reagent, and optionally at least one of buffers, salts, stabilizers and instructions.

DETAILED DESCRIPTION OF THE INVENTION

I. Definitions

Figure 1:
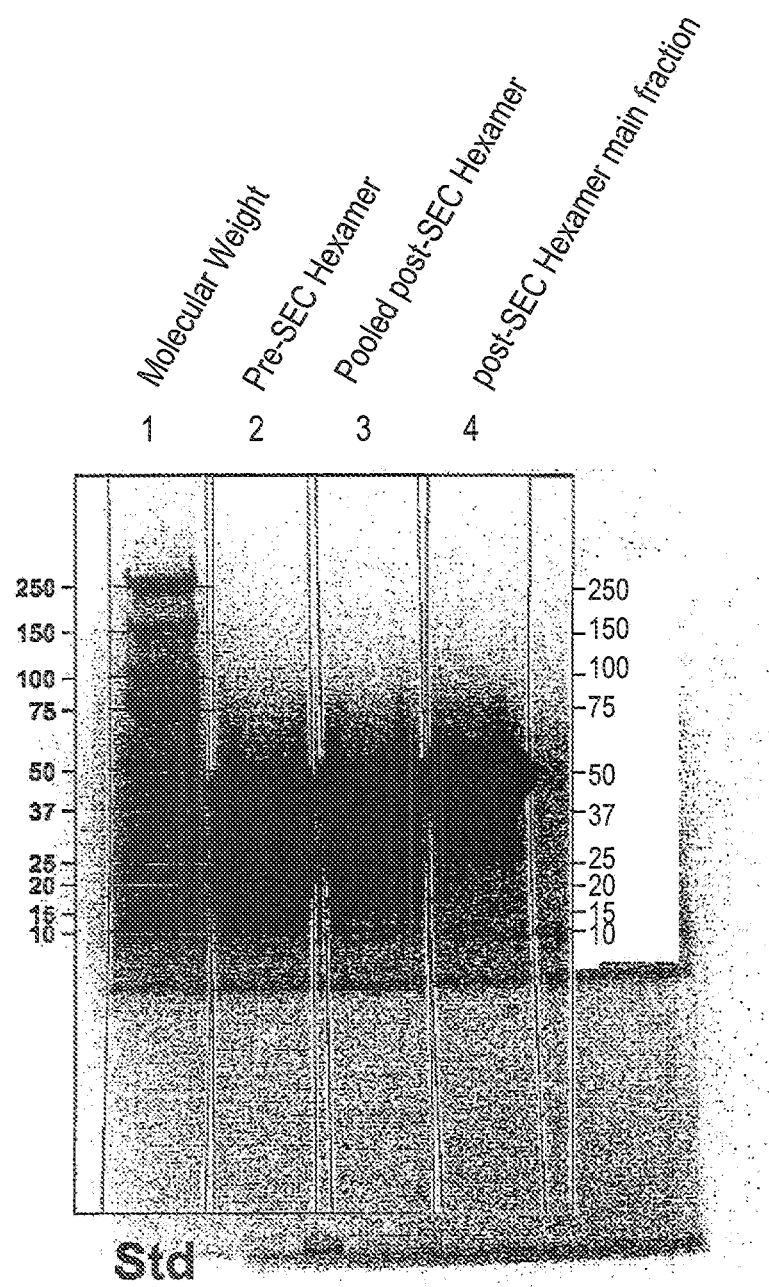
FIG. 1 shows purification of D2-hexamer.

As used herein, the term "contacting" refers to the process of bringing into contact at least two distinct species such that they can react. The resulting reaction product is either produced directly from a reaction between the added reagents or from an intermediate from one or more of the added reagents which can be produced in the reaction mixture.

As used herein, the term "bodily fluid" refers to fluids of a mammal including, but not limited to, aqueous humour, bile, blood and blood plasma, breast milk, interstitial fluid, lymph, mucus, pleural fluid, pus, saliva, serum, sweat, tears, urine, cerebrospinal fluid, synovial fluid or intracellular fluid. One of skill in the art will appreciate that other bodily fluids are useful in the present invention.

As used herein, the term "cross-linker" refers to a bifunctional or multi-functional chemical or biological moiety that is capable of linking two separate moieties together. Examples of cross-linkers useful in the present invention are described below.

As used herein, "antibody" includes reference to an immunoglobulin molecule immunologically reactive with a particular antigen, and includes both polyclonal and monoclonal antibodies.

As used herein, the term "subject" refers to animals such as mammals, including, but not limited to, primates (e.g., humans), cows, sheep, goats, horses, dogs, cats, rabbits, rats, mice and the like.

As used herein, the term "immobilized" refers to the association of the tTG, the gliadin fusion protein or the tTG-gliadin fusion protein complex with a solid support material through covalent bond formation, ionic bond formation, hydrogen-bonding, dipole-dipole interaction or via Van der Waals interactions. The immobilization can be temporary or permanent.

As used herein, the term "antigen" refers to a molecule that is capable of stimulating an immune response such as by production of antibodies. Antigens of the present invention include solid support immobilized gliadin fusion protein and solid support immobilized tTG-gliadin fusion protein complex. The gliadin fusion protein of the present invention can include both a recombinant deamidated gliadin and a tag, such as Glutathione S-transferase (GST) protein.

As used herein, the term "buffers" refers to any inorganic or organic acid or base that resists changes in pH and maintains the pH around a desired point. Buffering agents useful in the present invention include, but are not limited to, sodium hydroxide, dibasic sodium phosphate anhydrous, and mixtures thereof. One of skill in the art will appreciate that other buffering agents are useful in the present invention.

As used herein, the term "tissue Transglutaminase (tTG)" refers to an enzyme of the transglutaminase family that crosslinks proteins between an amino group of a lysine residue and a carboxamide group of a glutamine residue. This creates an intermolecular or intramolecular bond. tTG can be used to detect celiac disease.

As used herein, the term "gliadin fusion protein" refers to a gliadin protein linked to a tag, such as Glutathione S-transferase (GST) or a His tag. The gliadin protein includes a recombinant gliadin protein or a synthetic gliadin protein, among others. In some embodiments, the gliadin protein is deamidated. Tags are typically other proteins or compounds that can be used as affinity tags for purification, for solubilization, chromatography, as epitope tags, fluorescence tags, and others. Tags useful in the present invention include, but are not limited to, BCCP, c-myc-tag, Calmodulin-tag, FLAG-tag, HA-tag, His-tag, Maltose binding protein-tag, Nus-tag, Glutathione-S-transferase (GST) tag, Green fluorescent protein-tag. Thioredoxin-tag, S-tag, Streptag II, Softag 1, Softag 3, T7-tag, Elastin-like peptides, Chitin-binding domain, and Xylanase 10A. One of skill in the art will appreciate that other proteins are useful in fusion proteins of the present invention.

As used herein, the term "tTG-gliadin fusion protein complex" refers to a complex formed when the tTG and the gliadin fusion protein become linked together. The tTG and the gliadin fusion protein can be linked in a variety of ways, under a variety of reactions. The tTG can be linked to either or both of the tag and the recombinant deamidated gliadin of the gliadin fusion protein.

As used herein, the term "recombinant deamidated gliadin" refers to a deamidated gliadin protein prepared via genetic engineering. Deamidated proteins are those that have had some or all of the free amide functional groups hydrolyzed to carboxylic acids, such as conversion of glutamines to glutamic acid. In some embodiments, recombinant deamidated gliadins useful in the present invention comprise peptides having at least 75% sequence identity to SEQ ID NO:1 or comprise a hexamer having at least 75% sequence identity to SEQ ID NO:3.

As used herein, the term "crosslinked" refers to the formation of more than one bond between two different chemical moieties. In the present invention, the chemical moieties can be biological species such as proteins, enzymes, antibodies, etc., or solid support materials. The chemical functionality that links the individual chemical moieties that are crosslinked, is termed a "crosslinker". A crosslinker is typically a bifunctional compound that reacts with one reactive functional group on one chemical moiety and one reactive functional group on another chemical moiety, thereby linking the two chemical moieties to each other. The crosslinkers can be homobifunctional crosslinkers or heterobifunctional crosslinkers. Homobifunctional crosslinkers are those where the functional groups of the homobifunctional crosslinker that react with each chemical moiety are the same. Heterobifunctional crosslinkers are those where the functional groups of the heterobifunctional crosslinker that react with each chemical moiety are different. Preferred homobifunctional and heterobifunctional crosslinkers of the present invention are described in greater detail below.

As used herein, the terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 86%, 87%, 88%, 89%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition also refers to the complement of a test sequence.

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Delimit program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Preferred examples of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls of by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

As used herein, the terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate roam substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

As used herein, the phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to conform with codon preference in a specific host cell.

As used herein, the term "specifically bound" refers to the capturing or entrapment of the antigen of the present invention by an antibody that is indicative of the presence of celiac disease. Thus, under designated immunoassay conditions, an antibody (e.g., an anti-deamidated gliadin antibody) binds an antigen of the present invention at least two times over background level and more typically at least 5, 10, 20, 30, 40, or 50 times over background level. A variety of immunoassay formats may be used to determine whether an antibody specifically binds an antigen of the present invention. For example, solid-phase ELISA immunoassays are routinely used to determine whether an antibody is specifically immunoreactive with a protein (see, e.g., Harlow & Lane, Using Antibodies, A Laboratory Manual (1998) for a description of immunoassay formats and conditions that can be used to determine specific immunoreactivity).

II. Antigen

The present invention provides an antigen and method for detection of celiac disease. The antigen includes a gliadin fusion protein immobilized on a solid support material. The gliadin fusion protein includes both a recombinant deamidated gliadin and a tag. The antigen can optionally include tissue Transglutaminase (tTG). When present, the gliadin fusion protein and tTG can be covalently linked prior to immobilization on the solid support, such as via transamidation, to form a tTG-gliadin fusion protein complex. Following immobilization of the tTG-gliadin fusion protein complex on the solid support, the gliadin fusion protein and the tTG can be cross-linked using suitable cross-linkers.

In some embodiments, the present invention provides an antigen for detecting celiac disease. The antigen of the present invention includes the solid support bound gliadin fusion protein described below.

In other embodiments, the present invention provides an antigen for detecting celiac disease. The antigen includes a recombinant deamidated gliadin having a hexamer of peptides each having the sequence of SEQ ID NO:1, wherein the recombinant deamidated gliadin is covalently linked to a tag to form a gliadin fusion protein, wherein the gliadin fusion protein is immobilized on a solid support, and wherein the recombinant deamidated gliadin is capable of binding to anti-deamidated gliadin antibodies.

A. Gliadin Fusion Protein

The gliadin fusion protein useful in the present invention includes a recombinant deamidated gliadin that is expressed as a tagged protein. One of skill in the art will recognize that many recombinant gliadin proteins are useful in the method of the present invention. In some embodiments, the recombinant gliadin protein can include D2 (Aleanzi et al, Clin Chem 2001, 47 (11), 2023), peptide sequence: QPEQPQQS-FPEQERPF (SEQ ID NO:1). The recombinant gliadin protein can also include variants of D2, represented by the following formula:

$X^1PX^2X^3PX^4X^5SFPX^6X^7X^8RPF$     (SEQ ID NO: 12)

wherein each X is either glutamine (Q) or glutamic acid (E) such that at least one X is glutamine and at least one X is glutamic acid. The recombinant gliadin protein of the present invention can also be a hexamer of D2 or its variants. In some embodiments, the recombinant gliadin protein is a hexamer of D2 or its variants, separated by any suitable spacer, such as GGGGS (SEQ ID NO:2). One of skill in the art will appreciate that other spacers are useful in the present invention.

Any suitable spacer is useful in the present invention, and are interchangeable with linkers. Typical peptide spacer sequences contain Gly, Ser, Ala and Thr residues. Useful spacer include glycine-serine polymers including, for example, (GGGGS)n (SEQ NO:13), (GS)n, (GSGGS)n (SEQ ID NO:14), and (GGGS)n (SEQ ID NO:15), where n is an integer of at least one; glycine-alanine polymers; alanine-serine polymers; and other flexible linkers.

In some embodiments, the hexamer includes a spacer separating each peptide having the sequence of SEQ ID NO:1. In other embodiments, each spacer can have the sequence of SEQ ID NO:2.

In some embodiments, the recombinant deamidated gliadin is a D2 hexamer (SEQ ID NO:3). In some other embodiments, the present invention provides any nucleotide sequence that encodes the polypeptide in the sequence of SEQ ID NO:1 or SEQ ID NO:3. The recombinant deamidated gliadin proteins of the present invention bind to anti-deamidated gliadin antibodies, and are thus able to diagnose subjects having gluten related disorders such as celiac disease. One of skill in the art will appreciate that other recombinant deamidated gliadin proteins are useful in the present invention.

The gliadin fusion protein also includes a tag. Any tag known in the art is useful in the gliadin fusion proteins of the present invention. Tags suitable in the antigen of the present invention include, but are not limited to, a Glutathione S-transferase (GST), His-tag, FLAG, Streptag II, HA-tag, Softag 1, Softag 3, c-myc, T7-tag, S-tag, Elastin-like peptides, Chitin-binding domain, thioredoxin, Xylanase 10A, Maltose binding protein and NusA. In some embodiments, the tag is a Glutathione S-transferase (GST) or a His-tag. One of skill in the art will appreciate that other tags are useful in the present invention. The tag is typically attached to the recombinant gliadin protein via covalent linkage.

The His-tag useful in the present invention can be any suitable His-tag. His-tags suitable in the present invention include, but are not limited to, the sequence of SEQ ID NO:4, SEQ ID NO:5, or SEQ ID NO:6. In some embodiments, the His-tag can be the sequence of SEQ ID NO:5 or SEQ ID NO:6. In other embodiments, the recombinant deamidated gliadin can be the sequence of SEQ ID NO:7 or SEQ ID NO:8.

In another embodiment, the tag is a Glutathione S-transferase (GST) protein. The GST protein (SEQ ID NO:10) serves many functions, including enabling the purification of the recombinant gliadin protein and the presentation of epitopes represented in the recombinant gliadin protein.

When the gliadin fusion protein includes GST and the recombinant deamidated gliadin is the D2 hexamer, the gliadin fusion protein is represented by the sequence of SEQ ID NO:11. In some embodiments, the present invention provides any nucleotide sequence that encodes the polypeptide in the sequence of SEQ ID NO:11. The gliadin fusion protein of the present invention can be prepared by a variety of methods, including via recombinant methods such as those described.

Immobilization of the gliadin fusion protein on the solid support can be achieved by any method known in the art. The immobilization of the gliadin fusion protein to the solid support can be via covalent or ionic bond formation, hydrogen bonding, Van der Waals forces, as well as via antibody-antigen interactions. One of skill in the art will appreciate that other immobilization methods are useful in the present invention.

In some embodiments, the antigen also includes tissue Transglutaminase (tTG). When tTG is present, the tTG and gliadin fusion protein form a tTG-gliadin fusion protein complex. The tTG and the gliadin fusion protein can be linked in a variety of ways, such as by the formation of covalent bonds, ionic bonds, hydrogen bonding, or by Van der Waals interactions. When the tTG and the gliadin fusion protein are linked covalently, the covalent bonds can be formed by a variety of reactions, such as transamidation. The transamidation can occur under a variety of conditions, such as in the presence of $Ca^{2+}$. The tTG can be linked to either or both of the tag and the recombinant deamidated gliadin of the gliadin fusion protein. The tTG is immobilized to the solid support under the same conditions, and at the same time as immobilization of the gliadin fusion protein. Tissue transglutaminase is known to one of skill in the art and has been described previously, see NCBI RefSeq NP_004604 and NP_245189 (Apr. 13, 2008).

In other embodiments, the tTG and the gliadin fusion protein are covalently linked by a cross-linker. One of skill in the art will appreciate that other methods of cross-linking are available, such as via ionic bonding, hydrogen bonding or via van der Waals forces. One of skill in the art will recognize that any cross-linker is suitable in the instant invention. In some embodiments, the cross-linker is a member selected from the group consisting of a heterobifunctional crosslinker and a homobifunctional crosslinker. In yet other embodiments, the cross-linker is a homobifunctional crosslinker. In still yet other embodiments, the cross-linker is a member selected from the group consisting of bis(sulfosuccinimidyl)suberate (BS3), ethylene glycol bis[succinimidylsuccinate] (EGS), ethylene glycol bis[sulfosuccinimidylsuccinate] (sulfo-EGS), bis[2-(succinimidooxycarbonyloxy)ethyl]sulfone (BSOCOES), dithiobis(succinimidyl)propionate (DSP), 3,3'-dithiobis(sulfosuccinimidylpropionate) (DTSSP), disuccinimidyl suberate (DSS), disuccinimidyl glutarate (DSG), methyl N-succinimidyl adipate (MSA), disuccinimidyl tartarate (DST), 1,5-difluoro-2,4-dinitrobenzene (DFDNB), 1-ethyl-3-[3-dimethylaminopropyl]carbodiimide hydrochloride (EDC or EDAC), sulfosuccinimidyl-4-(N-maleimidomethyl)cyclohexane-1-carboxylate (sulfo-SMCC), N-hydroxysulfosuccinimide (sulfo-NHS), hydroxylamine and Sulfo-LC-SPDP (N-succinimidyl 3-(2-pyridyldithio)-propionate) and sulfo-succinimidyl 6-(3'-[2-pyridyldithio]-propionamido)hexanoate (sulfo-LC-SPDP). In another embodiment, the cross-linker is bis(sulfosuccinimidyl)suberate (BS3).

In a further embodiment, the recombinant deamidated gliadin has 95% identity to SEQ ID NO:3. One of skill in the art will appreciate that other percent identities are possible, such as 60% identity, preferably 65%, 70%, 75%, 80%, 85%, 86%, 87%, 88%, 89%, 90%, 91%, 92%, 93%, 94%, 95%, 96%, 97%, 98% or 99% identity over a specified region, when compared and aligned for maximum correspondence over a comparison window, or designated region. Such sequences are then said to be "substantially identical." The recombinant deamidated gliadin of the present invention having some percent identity to the sequence of SEQ ID NO:3 can bind to anti-gliadin antibodies in a sample in order to detect celiac disease. In some other embodiments, the recombinant deamidated gliadin has the sequence of SEQ ID NO:3.

B. Solid Support

A solid support material for use in the present invention is characterized by the following properties: (1) insolubility in liquid phases used for screening; (2) capable of mobility in three dimensions independent of all other supports; (3) containing many copies of the gliadin fusion protein or the tTG-gliadin fusion protein complex; (4) compatibility with screening assay conditions; and (5) being inert to the assay conditions. A preferred support also has reactive functional groups, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the gliadin fusion protein and tTG.

As used herein, solid support material is not limited to a specific type of support. Rather a large number of supports are available and are known to one of ordinary skill in the art. Solid phase supports include silica gels, resins, derivatized plastic films, beads such as glass, plastic, or magnetic beads, cotton, alumina gels, polysaccharides such as Sepharose and the like, etc. Other solid supports can be ELISA microtiter plates. A suitable solid phase support can be selected on the basis of desired end use and suitability for various synthetic protocols. For example, in polyamide synthesis, useful solid phase support can be resins such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories). Preferred solid phase synthesis supports for specific syntheses are described below. In some embodiments, the solid support is a bead. One of skill in the art will recognize that many types of solid supports are useful in the present invention.

C. Process for Preparing Recombinant Deamidated Gliadin Antigen

In some embodiments, the present invention provides an antigen for detecting celiac disease prepared by the process including contacting a solid support with a gliadin fusion protein, wherein the gliadin fusion protein includes a recombinant deamidated gliadin having a hexamer of peptides each having the sequence of SEQ ID NO:1 and wherein the recombinant deamidated gliadin is covalently linked to a tag, such that the gliadin fusion protein is immobilized on the solid support. Thus, the antigen for detecting celiac disease is prepared.

The process of preparing the recombinant deamidated gliadin antigen can prepare any recombinant deamidated gliadin antigen described above.

The tag is as described above. In some embodiments, the tag is GST or a His-tag. In another embodiment, the tag is GST. In some embodiments, the gliadin fusion protein is immobilized on the solid support via the tag.

The solid support is as described above. In some embodiments, the solid support is a bead, such as a magnetic head. In some embodiments, the solid support has a functional reactive group.

When tTG is present, the process can also include forming a covalent bond between the gliadin fusion protein and the tTG prior to the contacting step to form a tTG-gliadin fusion protein complex. The process of forming a covalent bond between the gliadin fusion protein and the tTG can also occur during and/or after the contacting step. The complexity of the gliadin fusion protein and the tTG can occur by any method known in the art. In some embodiments, the complexation occurs by transamidation to form a covalent bond.

In other embodiments, the process further comprises contacting the solid support with a cross-linker to cross-link the gliadin fusion protein and the tTG. In some other embodiments, the cross-linker cross-links the GST protein to the tTG. One of skill in the art will appreciate that any cross-linker is useful in the process of the present invention, such as those described above. The cross-linking can occur via hydrogen-bonding, covalent or ionic bond formation.

1. General Recombinant Methods

This invention can employ routine techniques in the field of recombinant genetics for the preparation of recombinant deamidated gliadin polypeptides. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999).

A recombinant deamidated gliadin, or a fusion protein, e.g., comprising recombinant deamidated gliadin and a tag such as a GST tag or a His tag, can be expressed using techniques well known in the art. Eukaryotic and prokaryotic host cells may be used such as animal cells, insect cells, bacteria, fungi, and yeasts. Methods for the use of host cells in expressing isolated nucleic acids are well known to those of skill and may be found, for example, in the general reference, supra. Accordingly, this invention also provides for host cells and expression vectors comprising the nucleic acid sequences described herein.

Nucleic acids encoding a recombinant deamidated gliadin, or a fusion protein, e.g., comprising recombinant deamidated gliadin and a to such as a GST tag or a His tag, can be made using standard recombinant or synthetic techniques. Nucleic acids may be RNA, DNA, or hybrids thereof. One of skill can construct a variety of clones containing functionally equivalent nucleic acids, such as nucleic acids that encode the same polypeptide. Cloning methodologies to accomplish these ends, and sequencing methods to verify the sequence of nucleic acids are well known in the art.

In some embodiments, the nucleic acids are synthesized in vitro. Deoxynucleotides may be synthesized chemically according to the solid phase phosphoramidite triester method described by Beaucage & Caruthers, *Tetrahedron Letts.* 22(20):1859-1862 (1981), using an automated synthesizer, e.g., as described in Needham-VanDevanter, et al., *Nucleic Acids Res.* 12:6159-6168 (1984). In other embodiments, the nucleic acids encoding the desired protein may be obtained by an amplification reaction, e.g., PCR.

One of skill will recognize many other ways of generating alterations or variants of a given polypeptide sequence. Most commonly, polypeptide sequences are altered by changing the corresponding nucleic acid sequence and expressing the polypeptide.

One of skill can select a desired nucleic acid or polypeptide of the invention based upon the sequences referred to herein and the knowledge readily available in the art regarding recombinant deamidated gliadin structure and function. The physical characteristics and general properties of these proteins are known to skilled practitioners.

To obtain high level expression of a recombinant deamidated gliadin, or a fusion protein comprising recombinant deamidated gliadin and a tag such as a GST tag or a His tag, an expression vector is constructed that includes such elements as a promoter to direct transcription, a transcription/translation terminator, a ribosome binding site for translational initiation, and the like. Suitable bacterial promoters are well known in the art and described, e.g., in the references providing expression cloning methods and protocols cited hereinabove. Bacterial expression systems for expressing ribonuclease are available in, e.g., *E. coli, Bacillus* sp., and *Salmonella* (see, also, Palva, et al., *Gene* 22:229-235 (1983); Mosbach, et al., *Nature* 302:543-545 (1983). Kits for such expression systems are commercially available. Eukaryotic expression systems for mammalian cells, yeast, and insect cells are well known in the art and are also commercially available.

In addition to the promoter, the expression vector typically contains a transcription unit or expression cassette that contains all the additional elements required for expression of the nucleic acid in host cells. A typical expression cassette thus contains a promoter operably linked to the nucleic acid sequence encoding the recombinant deamidated gliadin or the fusion protein (e.g., a recombinant deamidated gliadin-GST fusion protein), and signals required fox efficient polyadenylation of the transcript, ribosome binding sites, and translation termination. Depending on the expression system, the nucleic acid sequence encoding the recombinant deamidated gliadin or fusion protein (e.g., recombinant deamidated gliadin-GST fusion protein) may be linked to a cleavable signal peptide sequence to promote secretion of the encoded protein by the transformed cell.

As noted above, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET15b, pET23D, pET-22b(+), and fusion expression systems such as GST and LacZ. Epitope tags can also be added to recombinant proteins to provide convenient methods of isolation, e.g., 6-his. These vectors comprise, in addition to the expression cassette containing the coding sequence, the T7 promoter, transcription initiator and terminator, the pBR322 on site, a bla coding sequence and a lac1 operator.

The vectors comprising the nucleic acid sequences encoding the RNase molecules or the fusion proteins may be expressed in a variety of host cells, including E. coli, other bacterial hosts, yeast, and various higher eukaryotic cells such as the COS, CHO and HeLa cells lines and myeloma cell lines. In addition to cells, vectors may be expressed by transgenic animals, preferably sheep, goats and cattle. Typically, in this expression system, the recombinant protein is expressed in the transgenic animal's milk.

The expression vectors or plasmids of the invention can be transferred into the chosen host cell by well-known methods such as calcium chloride transformation for E. coli and calcium phosphate treatment, liposomal fusion or electroporation for mammalian cells. Cells transformed by the plasmids can be selected by resistance to antibiotics conferred by genes contained on the plasmids, such as the amp, gpt, neo and hyg genes.

Once expressed, the expressed protein can be purified according to standard procedures of the art, including ammonium sulfate precipitation, column chromatography (including affinity chromatography), gel electrophoresis and the like (see, generally, R. Scopes, *Protein Purification*, Springer-Verlag, N.Y. (1982), Deutscher, Methods in Enzymology Vol. 182: Guide to Protein Purification, Academic Press, Inc. N.Y. (1990); Sambrook and Ausubel, both supra.

In some embodiments, the present invention provides an isolated nucleic acid including the sequence of SEQ ID NO:9, which encodes a recombinant gliadin protein D2 hexamer sequence. In other embodiments, the isolated nucleic acid is in an expression vector. In some other embodiments, the expression vector is in a host cell.

2. Immobilization on the Solid Support

The gliadin fusion protein of the present invention can be immobilized to any useful solid support material by any useful immobilization method known in the art. The immobilization of the gliadin fusion protein to the solid support can be via covalent or ionic bond formation, hydrogen bonding, Van der Waals forces, as well as via antibody-antigen interactions. One of skill in the art will appreciate that other immobilization methods are useful in the present invention.

Other compounds have been developed that enable immobilization in a manner similar to antibodies. Certain of these "antibody mimics" use nonimmunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (*Proc. Natl. Acad. Sci. U.S.A.* 92(14):6552-6556 (1995)) discloses an alternative to antibodies based on cytochrome $b_{562}$. Ku et al. (1995) generated a library in which two of the loops of cytochrome $b_{562}$ were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins may be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96(5):1898-1903 (1999)) discloses an antibody mimic based on a lipocalin scaffold (ANTICALIN®). Lipocalins are composed of β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that ANTICALIN® would be suitable to be used as an alternative to antibodies.

ANTICALINS® are small, single chain peptides, typically between 160 and 180 residues, which provides several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of as peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49(2):209-216 (2003)) discusses a methodology for reducing antibodies into smaller peptidomimetics, which they term "antibody like binding peptidomemetics" (ABiP) which may also be useful as an alternative to antibodies.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Alternatively, known binding interactions between, for example, streptavidin and biotin, can be used to bind the gliadin fusion protein to the solid support.

Additional methods for linking the gliadin fusion protein to the solid support include the use of homobifunctional and heterobifunctional linkers. Zero-length cross linking reagents induce the direct conjugation of two ligands without the introduction of any extrinsic material. Agents that catalyze the formation of disulfide bonds belong in this category. Another example is reagents that induce the condensation of carboxy and primary amino groups to form an amide bond, such as carbodiimides, ethylchloroformate, Woodward's reagent K1, carbonyldiimidazole etc. Homobifunctional reagents carry two identical functional groups, whereas heterobifunctional reagents contain two dissimilar functional groups. A vast majority of the heterobifunctional cross-linking agents contains a primary amine-reactive group and a thiol-reactive group. A novel heterobifunctional linker for formyl to thiol coupling was disclosed by Heindel, N. D. et al., Bioconjugate Chem. 2, 427-430 (1991). In a preferred embodiment, the covalent cross-linking agents are selected from reagents capable of forming disulfide (—S—S—), glycol (—CH(OH)—CH(OH)—), azo (—N=N—), sulfone (—S(=O2)-), or ester (—C(=O)—O—) bridges.

Carboxylic acid groups residing on the surface of paramagnetic latex beads, internally dyed with Luminex dyes, can be converted to N-hydroxysuccinimide esters through the action of N-cyclohexyl-N'-(2-morpholinoethyl)carbodiimide metho-p-toluenesulfonate (CMC) and N-hydroxysuccinimide (NHS). After magnetic separation and washing, a mixture of the gliadin fusion protein and tTG is added in a detergent and buffered saline containing 10 mM $CaCl_2$ at pH 7.4. The suspension is incubated for 1 hour with shaking at room temperature. After washing, the beads are blocked to reduce non-specific binding and then stored in particle diluent.

III. Method for Diagnosing a Subject with Celiac Disease

In some embodiments, the present invention provides a method for diagnosing a subject with celiac disease. The method includes contacting a sample of bodily fluid from the subject with an antigen of the present invention, including a recombinant deamidated gliadin including a hexamer having the sequence of SEQ ID NO:3. The method also includes detecting any antibody that has become specifically bound to the antigen, thus indicating the presence of celiac disease in the subject.

The sample of the present invention can be any bodily fluid. In some embodiments, the sample can be aqueous humor, bile, blood and blood plasma, breast milk, interstitial fluid, lymph, mucus, pleural fluid, pus, saliva, serum, sweat, tears, urine, cerebrospinal fluid, synovial fluid or intracellular fluid. In some embodiments, the sample is a blood sample.

The subject of the present invention can be any mammal. In some embodiments, the subject can be primates (e.g., humans), cows, sheep, goats, horses, dogs, cats, rabbits, rats, mice and the like. In other embodiments, the subject is a human.

The presence of the antibody bound to the solid support immobilized gliadin fusion protein or tTG-gliadin fusion protein complex can be detected by any means known in the art. In some embodiments, the detecting step can be performed using an assay such as ELISA, a RIA or an immunofluorescence assay. In other embodiments, the detecting step can be performed using an enzymatic method. Immunoassays which can be used in the detecting step include, for example, competitive and non-competitive assay systems such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. See, e.g., Harlow and Lane, Using Antibodies, A Laboratory Manual, Cold Spring Harbor Laboratory, New York (1999).

The antibody specific for the antigen can be any suitable antibody. In some embodiments, the antibody can be IgA, IgD, IgE, IgG or IgM. In other embodiments, the antibody can be IgG or IgA. One of skill in the art will appreciate that other antibodies are useful in the present invention.

IV. Kits

In some embodiments, the present invention provides a kit including an antigen as described above, wherein the recombinant deamidated gliadin includes a hexamer that is substantially identical to the sequence of SEQ ID NO:3 or having the sequence of SEQ ID NO:3, a detection reagent, and optionally at least one of buffers, salts, stabilizers and instructions.

Buffers, salts and stabilizers useful in the present invention include those known to one of skill, and can be found in Gennaro, Ed., Remington's Pharmaceutical Sciences, $18^{th}$ Edition, Mack Publishing Co. (Easton, Pa.) 1990.

V. Examples

Example 1. Purification of D2-Hexamer with His Tag

The D2-hexamer with His tag can be purified using either native or denaturing conditions. In this example, the D2-hexamer was purified in the denaturing condition with 8M urea. A "classic" D2 hexamer with His tag was made in which the protein had the sequence of SEQ ID NO:7. Additionally, a "lysine-containing" D2 hexamer with His tag was made in which the protein had the sequence of SEQ ID NO:8.

Purification of the Classic Recombinant Hexamer.

The lysed cells from the 6 liter *E. coli* culture overexpressing the hexamer were suspended in the Equilibration Buffer (100 mM NaH2PO4, 8M Urea, 500 mM NaCl, 10 mM Imidazole, pH 8.0) at about 5 ml/g wet weight. After stirring for 30 min at room temperature, the cellular debris were removed by centrifugation. The about 200 ml supernatant was added to 25 ml of Ni-NTA resin pre-washed with the Equilibration Buffer, and mixed for 60 minutes at room temperature. The hexamer proteins bound to the resin were separated from the unbound lysate before being washed four times with 100 ml Washing Buffer (100 mM NaH2PO4, 8M urea, 500 mM NaCl, 20 mM imidazole, 0.5% Triton X100, pH 8.0). After the washing buffer was removed from the resin, the bound hexamer proteins were eluted with four volumes of 20 ml Elution Buffer (100 mM NaH2PO4, 8M urea, 200 mM NaCl, 250 mM imidazole, pH 7.5). The eluted protein fractions were pooled, concentrated, and dialysed against 10 mM MOPS, 150 mM NaCl (pH7.4). Any Precipitations observed were removed by centrifugation at 15 k×g. The affinity purified proteins can be further purified with a size-exclusion column with 10 mM MOPS, 150 mM NaCl (pH7.4), monitored with UV at 230 nm. The fractions containing the first main peak were pooled and concentrated.

The purification method of the lysine-containing D2-hexamer recombinant protein was identical to that of the classic recombinant hexamer.

Characterization of the Purified Classic or Lysine-Containing Hexamer Proteins.

The affinity purified protein was analyzed by SDS-PAGE gel electrophoresis (FIG. 1). The D2-hexamers that were further purified on the size-exclusion column as described above were analyzed by SDS-PAGE (FIG. 1). Unexpectedly, both hexamers (classic and the lysine-containing) showed a major band around 45 kd, corresponding to the size of a trimer of hexamer proteins. This aggregation of the hexamers is so strong that it is not dissociated under the denaturing conditions used in SDS-PAGE. Additionally, both hexamer proteins migrated at the position of about 45 kd in a size-exclusion chromatogram. Without being bound to a particular theory, the surprising tendency of the hexamers to aggregate to form a trimer of hexamers may contribute to the improved immunoreactivity of the D2 hexamer.

Example 2. Preparation of Recombinant Deamidated Gliadin Antigen

This example provides a protocol that was used for the preparation of the "classic" His-tagged recombinant deamidated gliadin protein (SEQ ID NO:7).

Immobilization of the Recombinant Deamidated Gliadin Peptide (DGP) Antigen on Magnetic Beads 10 mg of carboxyl modified magnetic beads are placed in a microfudge tube. 1000 µL of 50 mM 2-(N-morpholino) ethanesulfonic acid (MES) pH 6.1 in 70% ethanol (EtOH) is added to the tube. The tube is vortexed and beads are magnetically separated. The supernatant is pipetted off and discarded. This wash process is repeated one more time.

500 µL of 120 mM N-hydroxysuccinimide (NHS) in 50 mM MES, pH 6.1 in 70% EtOH is added into the tube with beads and mixed. 500 µL of N-Cyclohexyl-N'-(2-morpholinoethyl)carbodiimide metho-p-toluenesulfonate (CMC) in 50 mM MES, pH 6.1 in 70% EtOH is added into the same tube with beads and mixed. The tube is incubated at room temperature for 30 minutes while mixing continuously.

The beads are separated from the supernatant and 1000 µL of 5 mM MES pH 6.1 in 10% EtOH is added. The beads are mixed, magnetically separated and the supernatant pipetted off and discarded. This wash process is repeated one more time.

The washed beads are suspended by adding 250 µL of 5 mM MES pH 6.1 and mixed. The recombinant DGP antigen (prepared as detailed earlier) is mixed in the bead coupling buffer (buffered saline containing detergents) to obtain a coating concentration of 5 µg/mg, that is added to the beads. This mixture is incubated at room temperature for 60 minutes with continuous mixing.

1000 µL of post coating wash buffer (buffered saline containing detergents, calcium chloride and preservatives) is added to the tube and mixed. The beads are magnetically separated and the supernatant pipetted off and discarded. This wash process is repeated 3 more times.

Bead Blocking

1000 µL of blocking buffer (buffered saline containing detergents, calcium chloride, preservatives and blockers) added to the tube. The tube is incubated at 2-8° C. with mixing. The beads are magnetically separated and the supernatant pipetted off and discarded at the end of incubation.

The beads are washed with Particle diluent (buffered saline containing detergents, calcium chloride, preservatives and blockers) by adding 1000 µL of Particle diluent to the tube. The tube is mixed and the beads are magnetically separated and the supernatant pipetted off and discarded. This wash process is repeated 3 more times.

Add 1000 µL of Particle diluent (100 µL/mg particles) into the tube and store at 2-8° C. in this buffer.

Example 3. Detection of Celiac Disease Using the Recombinant DGP Antigen

This example provides a method that was used for the detection of celiac disease using the classic His-tagged recombinant deamidated gliadin protein (SEQ ID NO:7) as an antigen.

Summary of the Celiac IgA and IgG Immunoassay Protocol:

The instrument, BioPlex 2200 (manufactured by Bio-Rad Laboratories) aspirates 5 µL of sample from sample tube and dispenses it into a reaction vessel (RV) chased by 45 µL of Wash buffer (phosphate buffered saline containing detergent and preservatives).

100 µL of Sample diluent (buffered saline containing detergent, preservatives and Hookers) is added to the RV followed by 150 µL of Wash buffer.

The RV is incubated for 130 seconds at 37° C.

100 µL of Particle reagent (a solution of recombinant deamidated gliadin coated beads in particle diluent) is added to the RV. The final sample dilution is 1/80.

The mixture is incubated for 1180 seconds at 37° C. with intermittent mixing.

The beads are washed 3 times with 600 µL, then 300 µL, then 600 µL of Wash buffer with magnetic separation after each wash.

50 µL of Conjugate Reagent (a mixture of anti-human IgA/IgG-phycoerythrin in conjugate diluent (buffered saline containing detergent, preservatives and blockers)) is added to the RV.

The mixture is incubated for 600 seconds at 37° C. with intermittent mixing.

The beads are washed 3 times with 600 µL, then 300 µL, then 600 µL of Wash buffer with magnetic separation after each wash.

50 µL of Wash buffer is added to the RV to re-suspend the beads.

Figure 2:
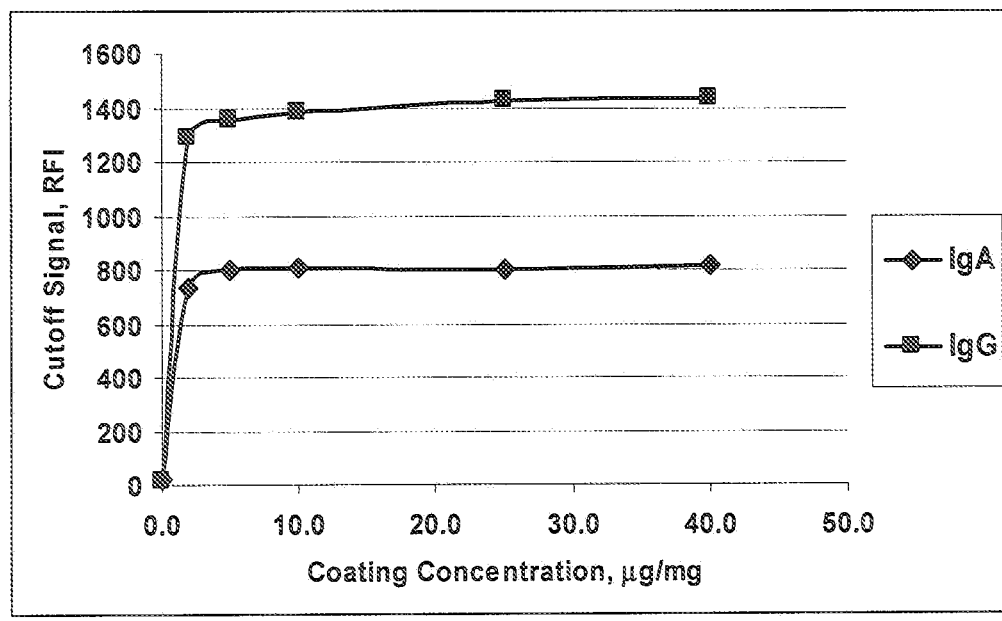
FIG. 2 shows coating titration of a DGP hexamer: Calibrator Cutoff signal relative fluorescence intensity (RFI).

The bead suspension is aspirated into the Luminex Detector module (LDM) and the median fluorescence of particles in each of the specified bead region is measured. FIG. 2 shows the coating titration of the DGP classic hexamer.

Sensitivity in Celiac Testing

Table 1 shows the amount of signal (relative fluorescence intensity, RFI) detected for normal and Celiac positive samples at different concentrations of DGP hexamer.

TABLE 1

RFI and Coating Concentration of DGP for "classic" DGP

| Coating Concentration | RFI of Normal healthy sample | | RFI of Celiac positive sample at cutoff | |
|---|---|---|---|---|
| of DGP, µg/mg | IgA | IgG | IgA | IgG |
| 0.0 | 21 | 14 | 20 | 15 |
| 2.0 | 46 | 71 | 750 | 1152 |

TABLE 1-continued

RFI and Coating Concentration of DGP for "classic" DGP

| Coating Concentration | RFI of Normal healthy sample | | RFI of Celiac positive sample at cutoff | |
|---|---|---|---|---|
| of DGP, µg/mg | IgA | IgG | IgA | IgG |
| 5.0 | 47 | 76 | 808 | 1235 |
| 10.0 | 49 | 81 | 831 | 1262 |
| 25.0 | 51 | 81 | 844 | 1273 |
| 40.0 | 50 | 80 | 842 | 1275 |

Analysis of Celiac Samples

The following concordance study was comprised of 62 Celiac samples. Table 2 shows the results of the comparison of DGP hexamer and the predicate method.

TABLE 2

Concordance study of 62 Celiac samples using "classic" DGP

| | Agreement with Predicate Method (INOVA) | | |
|---|---|---|---|
| Analyte | Positive agreement | Negative agreement | Total agreement |
| IgA | 97% | 91% | 95% |
| IgG | 100% | 94% | 97% |

Relative fluorescence intensity (RFI) was measured for normal and Celiac patient samples using a DGP hexamer (Table 3). Patient immunoreactivity was assessed by antibody index (AI) in which positive reactivity is >1.0.

TABLE 3

RFI and AI data for Normal and Celiac Patient samples using "classic" DGP

| Sample | RFI | AI |
|---|---|---|
| IgA | | |
| 2320644 | 170 | 0.2 |
| 2324881 | 49 | 0.0 |
| GA61882J | 956.0 | 2.1 |
| GA61882R | 903.0 | 1.5 |
| GA64089B | 809.0 | 1.6 |
| GA64089G | 1111.0 | 2.3 |
| GA64089O | 1753.5 | 3.6 |
| A-9355 | 42.0 | 0.0 |
| 15902.0 | 2030 | 4.5 |
| 16313 | 14928.0 | 20.1 |
| 13424 | 5724.0 | 8.1 |
| 13425 | 5816.0 | 8.2 |
| IgG | | |
| 2320644 | 37.0 | 0 |
| 2324881 | 75.0 | 0 |
| GG61791B | 1287.0 | 1.2 |
| GG61791J | 1319.0 | 1.3 |
| GG66322P | 204.0 | 0.2 |
| GG66322R | 3764.0 | 3.7 |
| GG66322T | 4847.0 | 4.2 |
| A-9355 | 105.0 | 0.1 |
| 15902 | 5360.0 | 4.5 |
| 16313 | 10454.0 | 8.5 |
| 13424 | 4436.0 | 3.3 |
| 13425 | 2171.5 | 1.9 |

Example 4. Detection of Celiac Disease Using the Recombinant DGP Antigen with an Additional Lysine In this example, the "lysine-containing" D2 hexamer protein (a His-tagged Recombinant Deamidated Gliadin Peptide with a lysine substituted for a glutamic acid residue at position 14 near the N-terminal region) (SEQ ID NO:8) was tested for sensitivity to Celiac disease.

Figure 3:
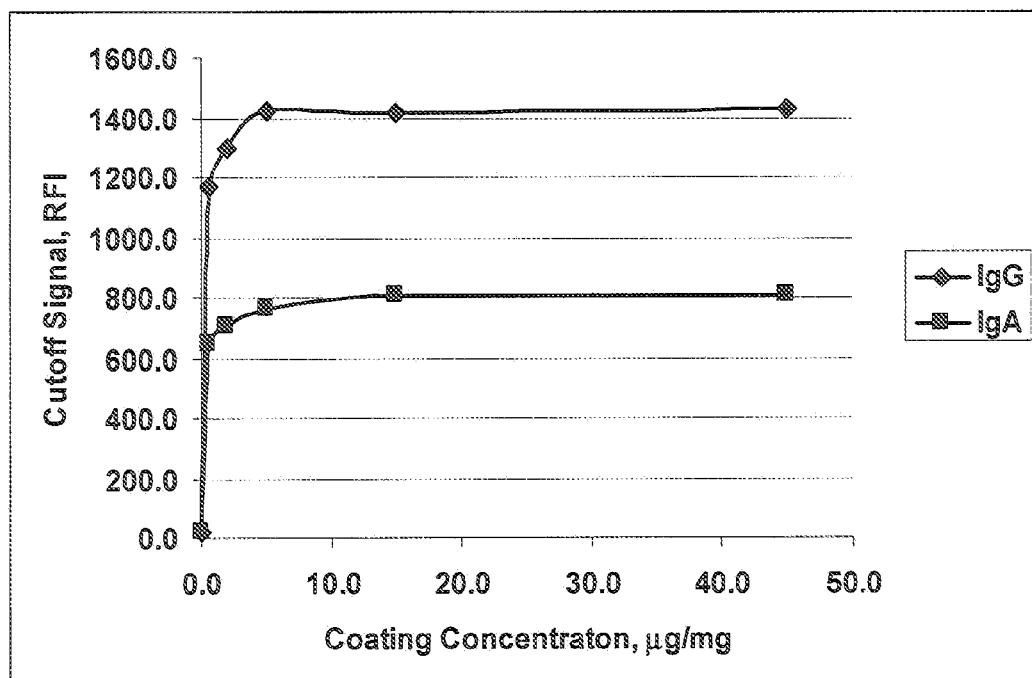
FIG. 3 shows coating titration of a DGP hexamer with a lysine substituted for the glutamic acid residue at position 14: Calibrator Cutoff signal RFI.

The immobilization of this antigen on magnetic beads was done in the same manner as described in Example 2. FIG. 3 shows the coating titration of the lysine-containing DGP hexamer.

The detection of Celiac disease using this antigen by immunoassay was performed in the same manner as described for the "classic" hexamer protein in Example 3.

Sensitivity in Celiac Testing

Table 4 shows the RFI for normal and Celiac positive samples at different concentrations of DGP hexamer.

TABLE 4

RFI and Coating Concentration of DGP for "lysine-containing" DGP

| Coating Concentration of | RFI of Normal healthy sample | | RFI of a Celiac positive sample at cutoff | |
|---|---|---|---|---|
| DGP, µg/mg | IgA | IgG | IgA | IgG |
| 0.0 | 21 | 22 | 25 | 27 |
| 0.5 | 45 | 60 | 623 | 1003 |
| 2.0 | 49 | 61 | 762 | 1170 |
| 5.0 | 61 | 89 | 814 | 1279 |
| 15.0 | 65 | 98 | 850 | 1336 |
| 45.0 | 64 | 95 | 875 | 1355 |

Analysis of Celiac Samples

Table 5 shows the relative fluorescence intensity (RFI) for normal and Celiac patient samples as measured by a DGP hexamer. Patient immunoreactivity was assessed by antibody index (AI) in which positive reactivity is >1.0.

TABLE 5

RFI and AI data for Normal and Celiac Patient samples using "lysine-containing" DGP

| Sample | RFI | AI |
|---|---|---|
| IgA | | |
| 2320644 | 165 | 0.2 |
| 2324881 | 55 | 0 |
| GA61882J | 942.0 | 2.1 |
| GA61882R | 814.0 | 1.5 |
| GA64089B | 749.5 | 1.6 |
| GA64089G | 1042.0 | 2.2 |
| GA64089O | 1647.0 | 3.5 |
| A-9355 | 45.0 | 0 |
| 15902.0 | 1920 | 4.5 |
| 16313 | 15549.0 | 23 |
| 13424 | 5407.0 | 8.2 |
| 13425 | 5587.5 | 8.4 |
| IgG | | |
| 2320644 | 47.0 | 0 |
| 2324881 | 70.0 | 0 |
| GG61791B | 1216.5 | 1.2 |
| GG61791J | 1120.0 | 1.1 |
| GG66322P | 194.0 | 0.2 |
| GG66322R | 3476.0 | 3.6 |
| GG66322T | 4607.0 | 4.2 |
| A-9355 | 153.5 | 0.1 |
| 15902 | 5541.0 | 4.6 |

TABLE 5-continued

RFI and AI data for Normal and Celiac Patient samples using "lysine-containing" DGP

| Sample | RFI | AI |
|---|---|---|
| 16313 | 10723 | 8.7 |
| 13424 | 3993.0 | 3.2 |
| 13425 | 1990.0 | 1.8 |

Example 5. Comparison Studies of DGP Trimer V. DGP Hexamer

The following concordance study consisting of 62 Celiac samples compared the predictive value of the DGP hexamer to a previously described gliadin antigen, a D2 trimer recombinant fusion protein (described previously in US 2009/0311727, incorporated by reference herein). The DGP hexamer showed improved positive agreement and total agreement versus DGP timer (Table 6). These results demonstrate the improved sensitivity of the DGP hexamer as compared to the DGP trimer.

TABLE 6

Comparison concordance study

| | Agreement with Predicate Method (INOVA) | | |
|---|---|---|---|
| Analyte | Positive agreement | Negative agreement | Total agreement |
| IgG-DGP Trimer | 84% | 94% | 89% |
| IgG-DGP Hexamer | 100% | 94% | 87% |

The DGP hexamer also showed surprisingly improved specificity as compared to the DGP trimer, which yielded many false positive results. This problem was eliminated by using the DGP hexamer.

Table 7 below shows data from a screen of 407 normal samples. DGP timer gave 25% false positives whereas DGP hexamer gave only 0.5% false positives. The specificity for false positive detection is ≤1%.

TABLE 7

| | Screen of normal samples | |
|---|---|---|
| | DGP Trimer | DGP Hexamer |
| Total Samples | 407 | 407 |
| False Positives | 102 | 2 |

Figure 4:
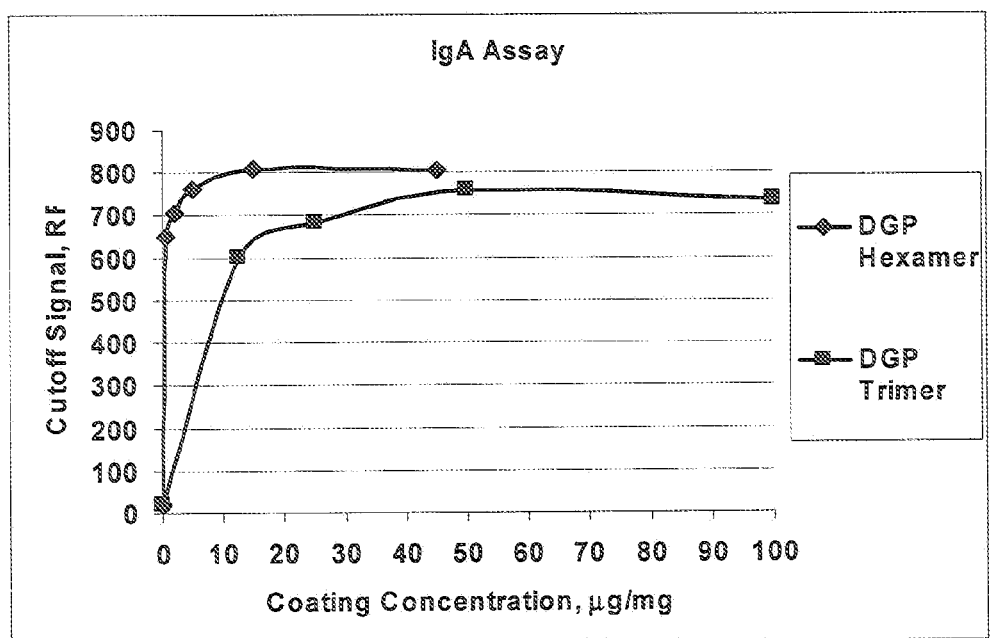
FIG. 4 shows the rDGP hexamer has improved sensitivity as compared to the rDGP trimer.
Figure 4:
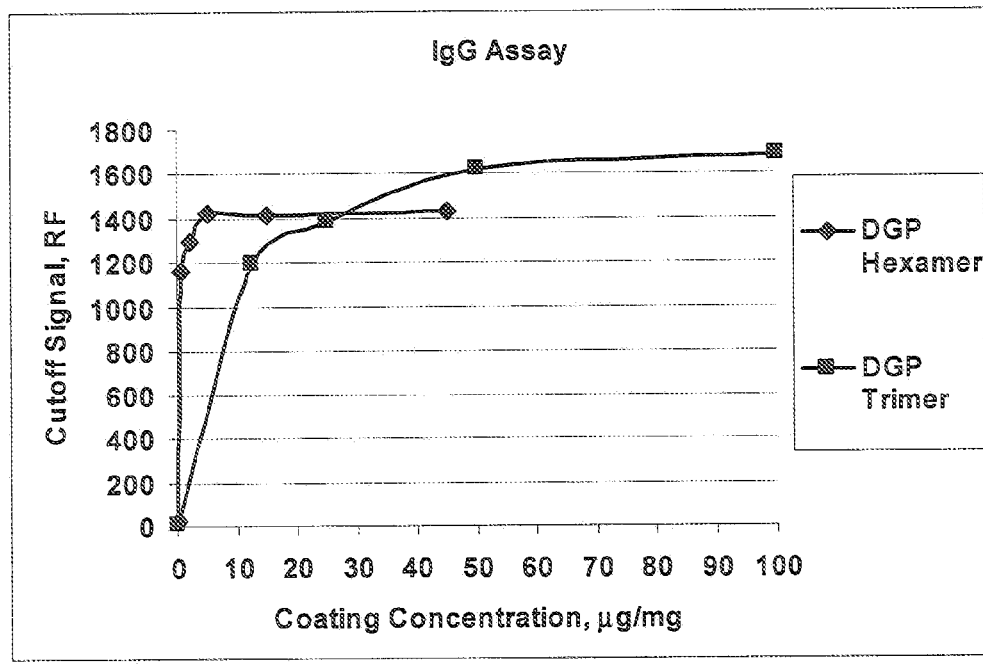

FIGS. 4a and 4b show the improved performance of the DGP hexamer as compared to the DGP trimer. In these studies, the bead coating concentration of the DGP hexamer was 5 times less than that of the DGP trimer, while the cutoff RFI signal was the same. The recombinant DGP hexamer had improved sensitivity as compared to the recombinant DGP trimer in both IgA (FIG. 4a) and IgG (FIG. 4b) assays.

Although the foregoing invention has been described in some detail by way of illustration and example for purposes of amity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An antigen for detecting celiac disease, the antigen comprising: a recombinant deamidated gliadin fusion protein consisting of SEQ ID NO:7 or SEQ ID NO:8; wherein the recombinant deamidated gliadin fusion protein is immobilized on a solid support and is capable of binding to anti-deamidated gliadin antibodies.

2. An antigen for detecting celiac disease prepared by the process comprising:
   contacting a solid support with a recombinant deamidated gliadin fusion protein consisting of SEQ ID NO:7 or SEQ ID NO:8 such that the recombinant deamidated gliadin fusion protein is immobilized on the solid support, thereby preparing the antigen for detecting celiac disease.

3. A method for diagnosing celiac disease in a subject, the method comprising: (a) contacting a sample of bodily fluid from the subject with the antigen of claim 1; (b) detecting any antibody that has become specifically bound to the antigen; and (c) indicating the presence of celiac disease in the subject when antibody is detected in (b).

4. The method of claim 3, wherein the sample is a blood sample.

5. The method of claim 3, wherein the detecting step is performed using an assay selected from the group consisting of ELISA, radioimmunoassay (RIA) and immunofluorescence assay.

6. The method of claim 3, wherein the antibody specific for the antigen is selected from the group consisting of IgG and IgA.

7. A kit comprising: the antigen of claim 1 and a detection reagent.

8. The kit of claim 7, wherein the kit further comprises at least one additional member selected from the group consisting of buffers, salts, stabilizers and instructions.

* * * * *